(12) United States Patent
Fischer

(10) Patent No.: US 7,569,185 B2
(45) Date of Patent: Aug. 4, 2009

(54) METHOD FOR INDICATING SHELF-LIFE AFTER MIXING PRE-DOSED, PRE-PACKAGED TWO-PART DENTAL COMPOSITIONS

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 204 days.

(21) Appl. No.: 11/537,807

(22) Filed: Oct. 2, 2006

(65) Prior Publication Data

US 2007/0106210 A1 May 10, 2007

Related U.S. Application Data

(63) Continuation-in-part of application No. 11/258,502, filed on Oct. 25, 2005, now abandoned, and a continuation-in-part of application No. 11/414,964, filed on May 1, 2006, now abandoned.

(51) Int. Cl.
*G01N 31/00* (2006.01)
*G01N 33/44* (2006.01)

(52) U.S. Cl. ............... 422/61; 422/58; 436/1; 436/2; 436/164; 436/165; 604/82; 424/10.1; 433/226

(58) Field of Classification Search ............ 422/55, 422/58, 61; 436/1–2, 164–165; 604/82; 424/10.1; 433/80, 226
See application file for complete search history.

(56) References Cited

U.S. PATENT DOCUMENTS

| | | | |
|---|---|---|---|
| 2,869,543 A | 1/1959 | Ratcliff et al. | 604/90 |
| 3,326,215 A | 6/1967 | Sarnoff et al. | 604/90 |
| 3,348,546 A | 10/1967 | Roberts et al. | 604/89 |
| 3,548,825 A | 12/1970 | Shaw | 604/91 |
| 3,685,514 A | 8/1972 | Cheney | 604/90 |
| 3,749,084 A | 7/1973 | Cucchiara | 600/575 |
| 3,872,864 A | 3/1975 | Allen, Jr. | 604/89 |
| 4,003,709 A | 1/1977 | Eaton et al. | 422/86 |
| 4,229,813 A | 10/1980 | Lilly et al. | 368/89 |

(Continued)

FOREIGN PATENT DOCUMENTS

CA 1158063 12/1983

(Continued)

OTHER PUBLICATIONS

Office Action dated Aug. 29, 2008 cited in U.S. Appl. No. 11/673,334.

*Primary Examiner*—Lyle A Alexander
(74) *Attorney, Agent, or Firm*—Workman Nydegger

(57) ABSTRACT

A pre-dosed, pre-packaged mixing system and associated method for mixing, storing, and dispensing a two-part dental composition that becomes less stable upon mixing. The mixing system includes a pre-dosed, pre-packaged quantity of a first component contained within a first chamber, and a pre-dosed, pre-packaged quantity of a second component contained within a second chamber. The chambers are separated by separation means so as to separate the two-components prior to mixing. Once mixed, the practitioner is able to record a mixing and/or expiration date on at least a portion of the mixing system so as to indicate a shelf-life of the less stable mixed dental composition.

26 Claims, 10 Drawing Sheets

U.S. PATENT DOCUMENTS

| | | | |
|---|---|---|---|
| 4,292,916 A | 10/1981 | Bradley et al. | 116/205 |
| 4,313,440 A | 2/1982 | Ashley | 604/191 |
| 4,412,836 A | 11/1983 | Brignola | |
| 4,463,875 A | 8/1984 | Tepic | |
| 4,464,174 A | 8/1984 | Ennis | 604/90 |
| 4,476,866 A | 10/1984 | Chin | 606/194 |
| 4,480,760 A | 11/1984 | Schonberger | 215/230 |
| 4,693,706 A | 9/1987 | Ennis, III | 604/87 |
| 4,743,229 A | 5/1988 | Chu | |
| 4,987,849 A | 1/1991 | Sherman | 116/206 |
| 5,032,178 A | 7/1991 | Cornell | 106/35 |
| 5,045,283 A | 9/1991 | Patel | 422/56 |
| 5,053,339 A | 10/1991 | Patel | 436/2 |
| 5,057,434 A | 10/1991 | Prusik et al. | |
| 5,228,573 A | 7/1993 | Pavelle et al. | 206/459.1 |
| 5,317,987 A | 6/1994 | Muller et al. | 116/206 |
| 5,354,285 A | 10/1994 | Mazurik et al. | 604/191 |
| 5,395,325 A | 3/1995 | Moreno et al. | 604/89 |
| 5,425,580 A | 6/1995 | Beller | |
| 5,429,603 A | 7/1995 | Morris | |
| 5,489,267 A | 2/1996 | Moreno et al. | 604/89 |
| 5,509,530 A | 4/1996 | Wilson | 206/220 |
| 5,534,562 A | 7/1996 | Jensen et al. | 523/118 |
| 5,633,836 A | 5/1997 | Langer et al. | 368/327 |
| 5,697,903 A | 12/1997 | Fischer | |
| 5,725,499 A | 3/1998 | Silverstein et al. | |
| 5,743,886 A | 4/1998 | Lynn et al. | 604/191 |
| 5,756,356 A | 5/1998 | Yanagi et al. | 436/7 |
| 5,802,015 A | 9/1998 | Rothschild et al. | 368/10 |
| 5,839,592 A | 11/1998 | Hayes | 215/230 |
| 5,876,372 A | 3/1999 | Grabenkort et al. | 604/89 |
| 5,908,054 A | 6/1999 | Safabash et al. | |
| 6,089,180 A | 7/2000 | Nichols, Jr. | 116/309 |
| 6,234,190 B1 * | 5/2001 | Fischer et al. | 137/68.23 |
| 6,331,076 B1 | 12/2001 | Coll | 374/102 |
| 6,501,390 B1 | 12/2002 | Chainer et al. | 340/870.16 |
| 6,540,072 B1 | 4/2003 | Fischer | |
| 6,715,645 B2 | 4/2004 | Peuker et al. | 222/129 |
| 6,743,194 B2 | 6/2004 | Sharon et al. | 604/89 |
| 6,818,682 B2 | 11/2004 | Falsafi et al. | 523/116 |
| 6,884,071 B2 | 4/2005 | Martin | 433/90 |
| 2003/0186196 A1 | 10/2003 | Wang et al. | 433/226 |
| 2004/0122359 A1 * | 6/2004 | Wenz et al. | 604/82 |
| 2005/0023173 A1 | 2/2005 | Paoletti | 206/459.5 |
| 2005/0177100 A1 | 8/2005 | Harper et al. | 604/89 |

FOREIGN PATENT DOCUMENTS

| | | |
|---|---|---|
| DE | 10021313 | 11/2001 |
| JP | 9182760 | 7/1997 |
| JP | 05104534 | 4/2005 |
| WO | WO9209870 | 6/1992 |
| WO | WO2005050192 | 6/2005 |

* cited by examiner

METHOD FOR INDICATING SHELF-LIFE AFTER MIXING PRE-DOSED, PRE-PACKAGED TWO-PART DENTAL COMPOSITIONS

RELATED APPLICATIONS

The present application is a continuation-in-part of copending U.S. patent application Ser. No. 11/258,502, filed Oct. 25, 2005 and entitled "TIME INDICATING CONTAINERS FOR DENTAL COMPOSITIONS, and a continuation-in-part of copending U.S. patent application Ser. No. 11/414,964, filed May 1, 2006 and entitled "TIME-INDICATING SYRINGE-IN-SYRINGE MIXING DEVICES AND RELATED METHODS FOR STORING AND DISPENSING TWO-PART DENTAL COMPOSITIONS, both of which are incorporated by reference in their entirety.

BACKGROUND OF THE INVENTION

1. The Field of the Invention

In one aspect, the present invention is directed to devices for holding and dispensing dental compositions. More particularly, in one aspect, the invention is directed to containers for holding and dispensing dental compositions having a given shelf-life after which the composition should either be used up or discarded. For example, many multi-part dental compositions require mixing of two separate components, the mixed composition having a particular shelf-life, after which time the mixed composition should be used up or discarded. Another aspect of the invention is related to methods for mixing such compositions and indicating shelf-life of the resulting compositions.

2. The Relevant Technology

Many modern formulations are packaged in two initially separate parts, often known as A and B components. Upon mixing, the A and B components form a mixed composition having a particular viable shelf-life, after which the composition should be used up or discarded. In the dental field, for example, several such formulations include two-part dental primers, peroxide and other two-part bleaching compositions, and disinfecting solutions.

It can be difficult for a dental practitioner to determine whether the shelf-life of a formulation has expired, or how much of the formulation's shelf-life remains. This difficulty can be further complicated in some instances where the shelf-life of a given formulation may depend on the environment in which the formulation is stored. For example, many formulations may have an extended shelf-life if stored in a refrigerated environment as compared to the shelf-life when stored at room temperature.

Furthermore, when mixing a two-part composition it is necessary to measure needed amounts of each component. In addition to being tedious, even small variations in measurement of one component relative to another component may drastically affect the actual shelf-life of the mixed composition because of errors in the mixing ratio of the components.

It would be an advantage to provide a container system for use with such a formulation that would allow the user to quickly and easily determine how much time remains of the shelf-life of a given formulation. It would be a further advantage if such a system could account for variability in shelf-life due to changes in the formulation storage environment. It would be a further advantage to provide a simple method that would indicate remaining shelf-life of a composition, and that would eliminate variability in actual shelf-life due to errors in measuring needed quantities of the components.

SUMMARY OF THE INVENTION

In one aspect, the present invention is directed to a storage system for a dental composition having a given shelf-life. The storage system includes a container (e.g., a syringe), and activatable time sensitive marking means disposed on or within the container, wherein upon activation, the time sensitive marking means identifies time lapsed since activation of the time sensitive marking means. The dental practitioner may activate the time sensitive marking means at an appropriate time to monitor the shelf-life of the dental composition (e.g., immediately after preparing the composition by mixing together initially separate components). The time sensitive marking means allows a dental practitioner to determine whether a dental composition within the container has expired, or how much time remains before the composition expires and should either be used up or discarded.

In one example, the activatable time sensitive marking means comprises an activatable label disposed on or within the container. One such label includes a length of a microporous material and a tinted liquid that migrates along the microporous material by capillary action so as to have a migration length that increases as a function of time. The label is activated by causing the tinted liquid to contact the microporous material. In one example, the tinted liquid may initially be contained within a blister or similar packaging adjacent to the microporous material. Upon pressing (i.e., activating) the blister packaging, the tinted liquid contacts the microporous material and begins to wick up along the microporous material due to capillary action. The progress of the tinted liquid is a function of time, such that the migration length of the tinted liquid indicates how much time has lapsed since activation (and thus also the time remaining until the shelf-life of the composition expires).

In another example, the activatable time sensitive marking means may comprise a label including two adjacent blister packets, each blister packet containing a composition such that the compositions are initially separate from each other. The user presses one or both of the blisters so as to cause a thin membrane between the blister packets to break, which allows the two compositions to mix together, activating the label. The mixed composition begins as characterized by having a first color, and progressively changes to a second color as a function of time. Once the mixed composition has changed to the second color, this indicates to the user that the given shelf-life of a dental composition within the container has expired and should be discarded.

Another activatable time sensitive marking means may comprise a tape formed of a material that begins to change color from a first color to a second color as a function of time. Once the tape has changed to the second color, this indicates to the user that the given shelf-life of a dental composition within the container has expired.

Another activatable time sensitive marking means may comprise a label including a microchip configured to measure lapsed time. The microchip is readable by an associated microchip reader so as to indicate to a user how much time remains of a given shelf-life of a composition within the container.

The activatable time sensitive marking means may be temperature sensitive in addition to being time sensitive. Temperature sensitivity of the marking means allows the system to account for variability in shelf-life due to temperature changes in the storage environment of the dental composition stored within the container.

A dental composition within the container may have a given shelf-life ranging from less than about a week to 2 years or more. Because of relative instability, many mixed two-part dental compositions have a relatively short shelf-life (e.g., 30 days or less). For example some two-part peroxide bleaching compositions may have a shelf-life of about 10-14 days after mixing, some disinfecting solutions may have a shelf-life of about a week or less, and some two-part dental primers may have a shelf life of about 30 days. Relatively stable single part dental compositions may have a longer shelf-life (e.g., from 6 months up to 2 years or more). Such compositions often include an expiration date stamped or printed on the container, which can be difficult to identify. The time sensitive marking means of the present invention provides a more easily identifiable label, eliminating the need for the user to search for a difficult to find date stamp.

In another aspect, the present invention is directed to a pre-dosed, pre-packaged mixing solution that includes the two-components in an initially separate configuration, and an associated method in which the dental practitioner is able to record a mixing and/or expiration date of the less stable mixed composition on the mixing system itself. The mixing system includes a pre-dosed, pre-packaged quantity of a first component contained within a first chamber, and a pre-dosed, pre-packaged quantity of a second component contained within a second chamber. The chambers are separated by separation means so as to separate the two-components prior to mixing. Once mixed, the practitioner is able to record a mixing and/or expiration date on at least a portion of the mixing system so as to indicate the shelf-life of the less stable mixed composition.

Providing a pre-dosed, pre-packaged mixing system advantageously eliminates any need for the dental practitioner to measure the required quantities of each component prior to preparing the two-part composition. In addition to being convenient, because the pre-dosing is done during manufacture, it is advantageously accomplished with a greater degree of precision and accuracy than possible in the dental office environment. This reduces or eliminates the possibility of mistakes or errors in the measured quantities of each component, which affects the mixing ratio of the two components. This is particularly helpful as errors in the mixing ratio may drastically affect the actual shelf-life of the mixed composition. For example, a mixed dental priming composition may have a nominal shelf-life of about 30 days after mixing, but because of a small error (e.g., ±10%) in mixing ratio, the actual shelf-life of the composition may be greatly reduced (e.g., to less than 15 days). If the composition is used after its actual expiration date but before the nominal expiration date, the composition will be ineffective, resulting in waste and frustration to the dental practitioner and patient. In other words, the indicated expiration date is much more meaningful in the context of a pre-dosed, pre-packaged mixing system as compared to any other system where individual measurement of one or more of the components is required.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction

A detailed description of the invention will now be provided with specific reference to figures illustrating various exemplary embodiments. It will be appreciated that like structures will be provided with like reference designations.

In one aspect, the present invention is directed to a storage system for dental compositions having a given shelf-life. The storage system includes a container (e.g., a syringe) and an activatable time sensitive marking means disposed on or within the container. Upon activation, the time sensitive marking means begins to indicate time lapsed since activation of the time sensitive marking means. The dental practitioner may activate the time sensitive marking means at an appropriate time to allow the dental practitioner to monitor the shelf-life of the dental composition (e.g., immediately subsequent to preparing the composition by mixing together initially separate components, exposing the dental composition to air, or exposing the dental composition to light). The time sensitive marking means allows a dental practitioner to determine whether a dental composition within the container has expired, or how much time remains before the composition expires and should be used up or discarded. The container and activatable time sensitive marking means may be relatively inexpensive, allowing the user to discard the entire system once the dental composition has expired.

In another aspect, the present invention is directed to a pre-dosed, pre-packaged mixing solution that includes the two-components in an initially separate configuration, and an associated method in which the dental practitioner is easily able to record a mixing and/or expiration date of the mixed, less stable dental composition on the mixing system itself. The mixing system includes a pre-dosed, pre-packaged quantity of a first component contained within a first chamber, and a pre-dosed, pre-packaged quantity of a second component contained within a second chamber. The chambers are separated by separation means so as to separate the two-components prior to mixing. Once mixed, the practitioner is able to record a mixing and/or expiration date on at least a portion of the mixing system so as to indicate when a shelf-life of the less stable mixed composition expires.

II. Exemplary Dental Composition Container Systems

Figure 1A:
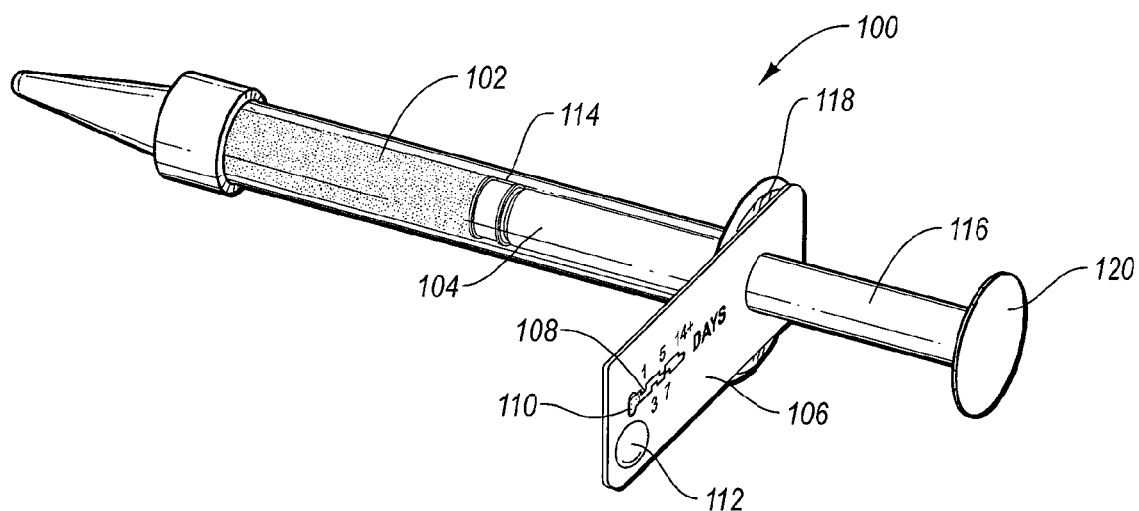
FIG. 1A is a perspective view of an exemplary time indicating system for containing a dental composition including a syringe and an activatable time sensitive label disposed on the syringe plunger stem.

FIG. 1A illustrates an exemplary system 100 for both containing and dispensing a dental composition 102. System 100 includes a syringe 104 and an activatable time sensitive label 106. Syringe 104 includes a barrel 114 and a plunger 116. Barrel 114 includes a flange 118 and plunger 116 includes a head 120. Label 106 includes a length of a microporous material 108 and a tinted liquid 110 that is initially contained within a blister 112. In the illustrated system, label 106 includes a hole through which the plunger 116 of syringe 104 passes. Label 106 may be adhered to flange 118 of syringe 104 or may slide with plunger 116.

Label 106 is activated by causing the tinted liquid to contact the microporous material. In one example, the tinted liquid may initially be contained within a blister or similar packaging adjacent to the microporous material. Upon pressing (i.e., activating) the blister packaging, the tinted liquid contacts the microporous material and begins to wick up along the microporous material due to capillary action. The progress of the tinted liquid is a function of time, such that the migration length of the tinted liquid (i.e., how far along the microporous material the tinted liquid has migrated) indicates how much time has lapsed since activation (and thus also the time remaining until the shelf-life of the composition expires). As illustrated, microporous material 108 may include markings spaced along its length to mark how much time has lapsed since activation (e.g., a number of days, weeks, or months) when the tinted liquid reaches the corresponding mark. One such activatable label including a microporous material and a tinted liquid initially contained within a blister that may be suitable is available from Timestrip Ltd., located in Hitchin, Hertfordshire, United Kingdom.

Figure 1B:
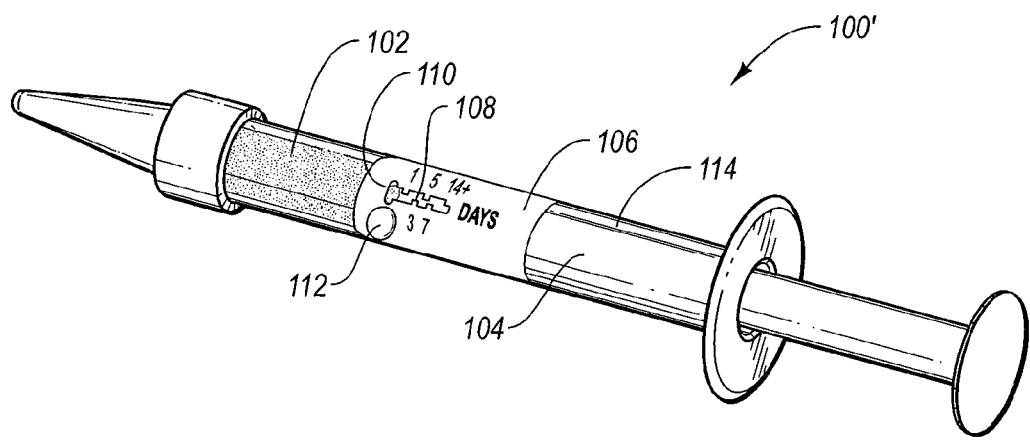
FIG. 1B is a perspective view of another exemplary time indicating container system including a syringe and an activatable time sensitive label disposed on the syringe barrel.

FIG. 1B illustrates an alternative system 100' including a syringe 104 containing a dental composition 102 and a label 106 adhered to the barrel 114 of syringe 104. Label 106 includes a length of a microporous material 108 and a tinted liquid 110 that is initially contained within a blister 112. Upon pressing (i.e., activating) blister 112, the tinted liquid 110 is brought into contact with the microporous material 108 and begins to wick up along the microporous material 108 due to capillary action. The progress of the tinted liquid 110 indicates how much time has lapsed since activation.

Figure 1C:
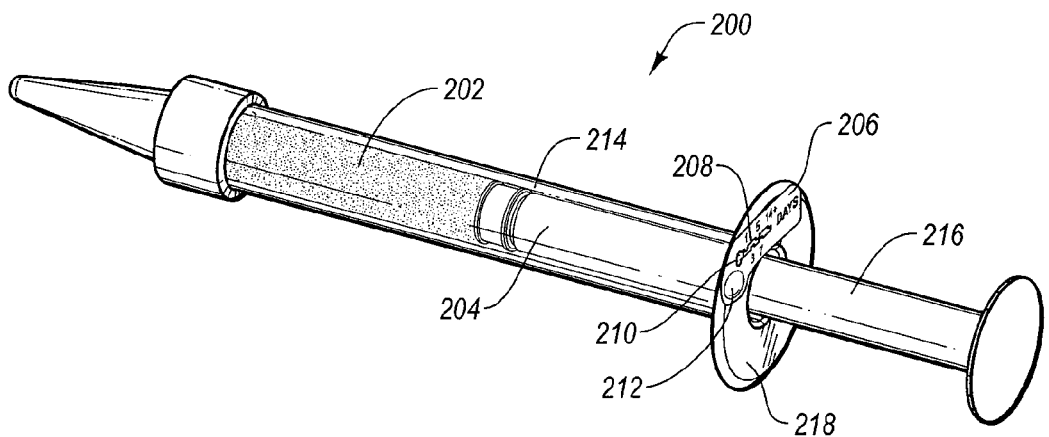
FIG. 1C is a perspective view of another exemplary time indicating container system including a syringe and an activatable time sensitive label disposed on the syringe barrel flange.

FIG. 1C illustrates an alternative system 200 including a syringe 204 containing a dental composition 202 and a label 206 adhered to flange 218 of syringe barrel 214. Label 206 includes a length of a microporous material 208 and a tinted liquid 210 that is initially contained within a blister 212. Upon pressing (i.e., activating) blister 212, the tinted liquid 210 is brought into contact with the microporous material 208 and begins to wick up along the microporous material 208 due to capillary action. The progress of the tinted liquid 210 indicates how much time has lapsed since activation.

Figure 1D:
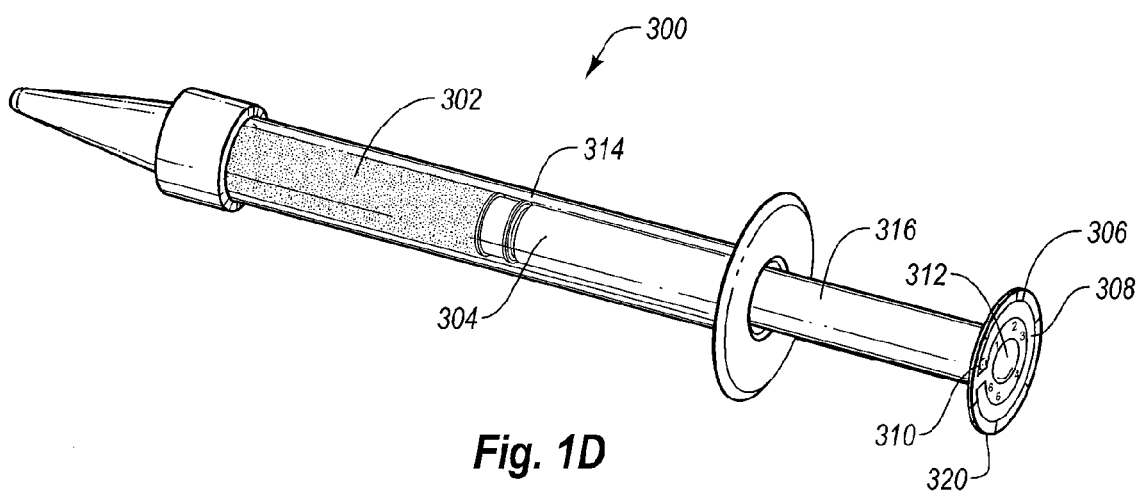
FIG. 1D is a perspective view of another exemplary time indicating container system including a syringe and an activatable time sensitive label disposed on the head of the plunger stem.

FIG. 1D illustrates an alternative system 300 including a syringe 304 containing a dental composition 302. Syringe 304 includes a barrel 314 and a plunger 316. A label 306 is disposed on head 320 of plunger 316. Label 306 includes a curved length of microporous material 308 and a tinted liquid 310 that is initially contained within blister 312. A substantially straight length of microporous material may alternatively be used. In addition, a curved length of microporous material 308 may also be used with any of the other illustrated embodiments. Such a curved length of microporous material 308 may be particularly suited for the embodiment of FIG. 1C.

Again referring to FIG. 1D, locating blister 312 on head 320 makes it conveniently placed for activation as plunger 316 is also used to dispense composition 302. Blister 312 can be pressed, forcing tinted liquid 310 into contact with an end of the curve of microporous material 308. Liquid 310 begins to wick up, progressing along microporous material 308 due to capillary action. The progress of the tinted liquid 310 indicates how much time has lapsed since activation under given conditions (e.g., room temperature).

Figure 1E:
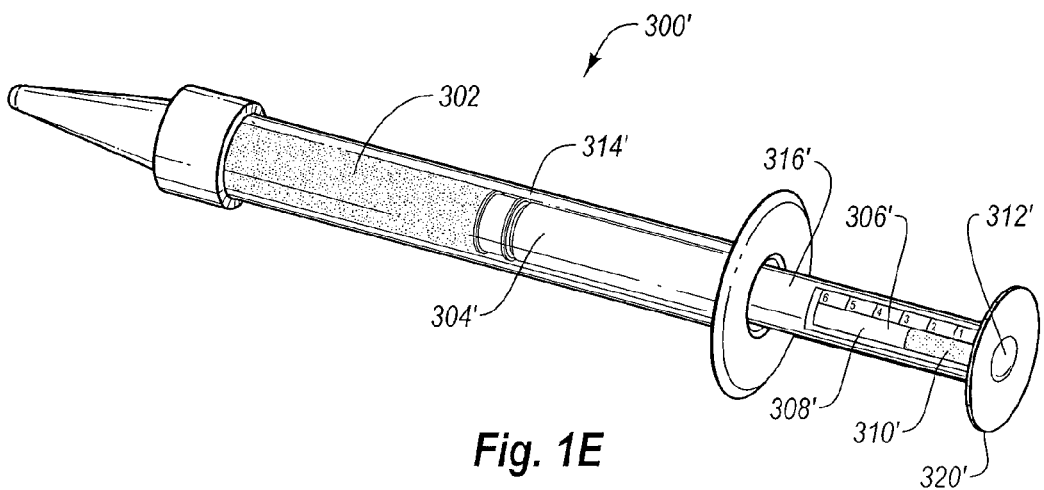
FIG. 1E is a perspective view of another exemplary time indicating container system including a syringe and an activatable time sensitive label disposed at least partially within the plunger stem of the syringe.

FIG. 1E illustrates an alternative system 300' including a syringe 304' containing a dental composition 302. Syringe 304' includes a barrel 314 and a plunger stem 316'. A label 306' is disposed at least partially within plunger 316'. Label 306' includes a length of microporous material 308' that is sealed within plunger stem 316'. Microporous material 308' is arranged so as to be along or parallel to the central longitudinal axis of plunger stem 316'. A tinted liquid 310' is initially contained within blister 312' disposed on head 320'. Blister 312' can be pressed, forcing tinted liquid 310' into contact with an end of microporous material 308'. Liquid 310' begins to wick up, progressing along microporous material 308' due to capillary action. The progress of the tinted liquid 310' indicates how much time has lapsed since activation under given conditions (e.g., room temperature). Sealing microporous material 308' within plunger stem 316' provides a controlled humidity environment for microporous material 308', which can provide increased accuracy when used in both dry and humid environments where humidity may not be constant. This is because the rate of progress along the microporous material due to capillary action can be affected by changes in humidity.

Labels 106, 206, 306, and 306' are examples of activatable time sensitive marking means. Because the labels rely on capillary action of a liquid migrating through a microporous material, the rate of migration of the tinted liquid may be dependent on temperature in addition to time. In other words, the tinted liquid may migrate a given distance (e.g., about the distance marked "7 days") over a seven day period when stored at room temperature, but may alternatively migrate a shorter distance (e.g., about the distance marked "3 days") if stored in a refrigerated environment (e.g., as a result of increased viscosity of the tinted liquid and/or decreased wetting ability of the microporous material). Surprisingly, it has been found that the temperature dependent variability of the capillary action roughly matches the temperature dependent variability of the shelf-life of many dental compositions. For example, the dental composition may be stored in a refrigerated environment, and then later stored at room temperature, and the progress of the tinted liquid along the microporous material may vary according to the environment conditions. This characteristic is advantageous as it allows the label to accurately indicate the remaining shelf-life of a dental composition that varies due to differences in storage environments.

Figure 2:
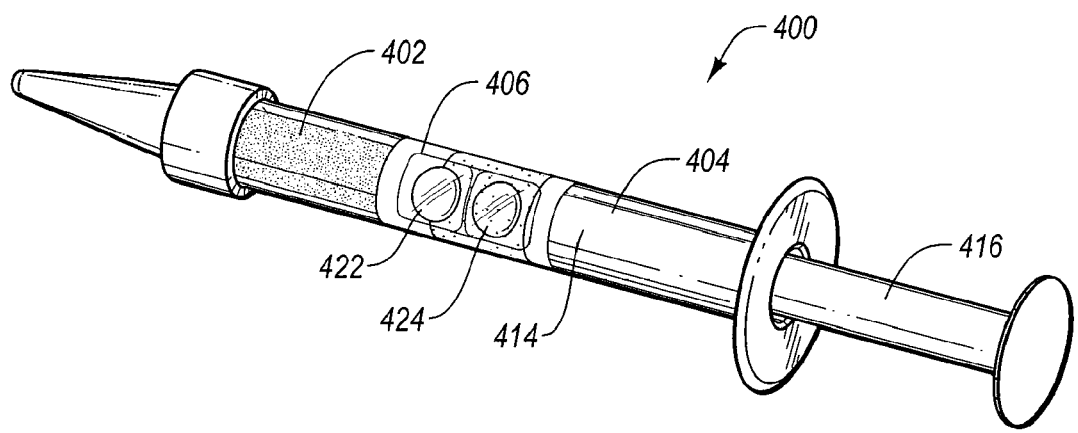
FIG. 2 illustrates a time indicating container system including a syringe and an activatable time sensitive label having two blister packets for forming a color changing composition.

FIG. 2 illustrates an alternative system 400 including a syringe 404 containing a dental composition 402. Syringe 404 includes a barrel 414 and a plunger 416. A label 406 is disposed on barrel 414. Label 406 includes a first blister 422 and a second blister 424 near first blister 422. First blister 422 contains a first composition and second blister 424 contains a different second composition. Blisters 422 and 424 are initially separated by a thin membrane. In order to activate time sensitive label 406, the user presses one or both of blisters 422 and 424 so as to break the thin membrane and cause the compositions to mix together. The mixed composition begins as a first color and progressively changes to a second different color over time. As long as the mixed composition is not of the second color, the user knows that the dental composition within container has not yet expired. Once the second color has been reached, the dental composition 402 or system 400 should be discarded. In some embodiments, the mixed composition may include one or more intermediate colors between the initial color and the second color that signifies expiration of the dental composition. One such label including blisters containing initially separate components for forming a color changing mixed composition that may be suitable is available from Vitsab Inc., located in Belmont, N.C.

Because label 406 relies on a color changing chemical reaction, the rate of reaction may also be dependent on temperature. Surprisingly, it has been found that the temperature dependent variability of the color changing chemical reaction roughly matches the temperature dependent variability of the shelf-life of many dental compositions. This characteristic is advantageous as it allows the label to accurately indicate the remaining shelf-life of a dental composition that varies due to differences in storage environments.

Figure 3:
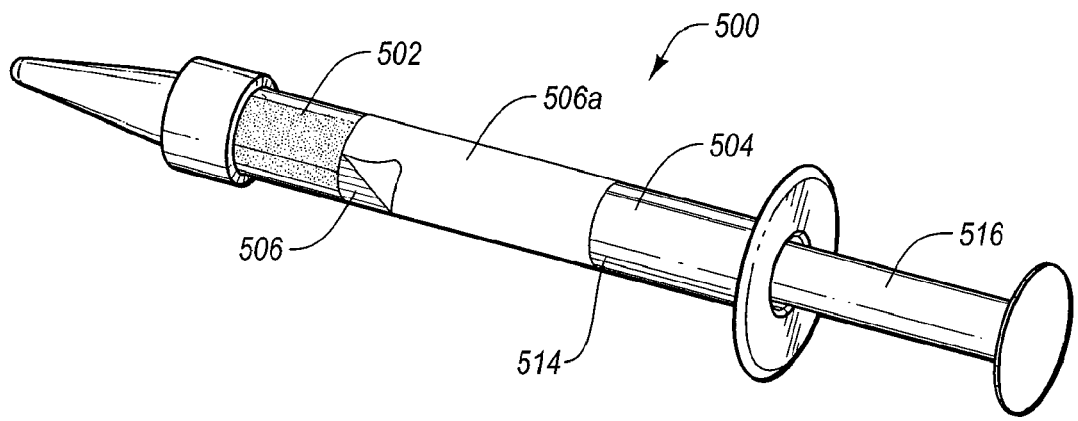
FIG. 3 illustrates a time indicating container system including a syringe and a color changing tape disposed on the syringe barrel.

FIG. 3 illustrates an alternative system 500 including a syringe 504 containing a dental composition 502. Syringe 504 includes a barrel 514 and a plunger 516. A label 506 is disposed on barrel 514. Label 506 is formed of a material that begins to change color from a first color to a second color as a function of time. After activation, as long as label 506 is not of the second color, the user knows that the dental composition 502 within container 504 has not yet expired. Once the second color has been reached, the dental composition 502 or system 500 should be discarded. In some embodiments, the label 506 may change colors so as to include one or more intermediate colors between the initial color and the second color that signifies expiration of the dental composition. One such label formed of a color changing material that may be suitable is available from Wipak UK Ltd., located in Welshpool, Powys, United Kingdom.

Label 506 may be activated by exposure of the material to moisture within the air. As such, label 506 may initially include a peelable moisture barrier foil 506a that covers label 506. In order to activate label 506, the user simply removes foil 506a.

Because label 506 relies on a color changing chemical reaction, the rate of reaction may also be dependent on temperature. Surprisingly, it has been found that the temperature dependent variability of the color changing chemical reaction roughly matches the temperature dependent variability of the shelf-life of many dental compositions. This characteristic is advantageous as it allows the label to accurately indicate the remaining shelf-life of a dental composition that varies due to differences in storage environments.

Figure 4:
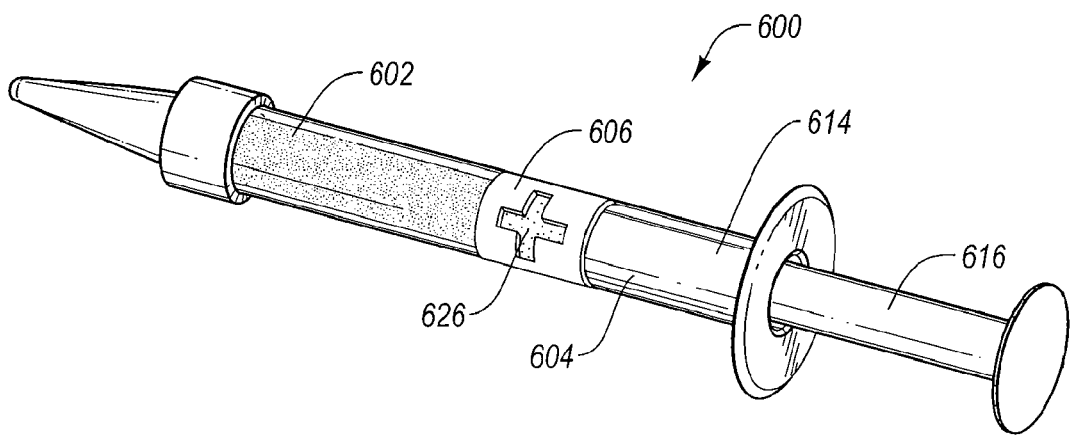
FIG. 4 illustrates a time indicating container system including a syringe and an activatable label including a machine readable time monitoring microchip.

FIG. 4 illustrates an alternative system 600 including a syringe 604 containing a dental composition 602. Syringe 604 includes a barrel 614 and a plunger 616. A label 606 is disposed on barrel 614. Label 606 includes a microchip 626 configured to measure lapsed time. Microchip 626 is readable by an associated microchip reader so as to indicate to a user how much time remains in the shelf-life of composition 602 within container 604. One such label including a microchip configured to measure lapsed time and an associated microchip reading device that may be suitable is available from Clinisense Corporation located in Los Gatos, Calif.

Microchip 626 may also be configured to account for differences in temperature, so as to integrate monitoring of both time and temperature. Such a configuration allows the label to accurately indicate the remaining shelf-life of a dental composition that is stored in a variety of environments.

The dental composition within the syringe or other container may have a given shelf-life ranging from less than about a week to 2 years or more. Because of relative instability many mixed two-part dental compositions have a relatively short shelf-life (e.g., 30 days or less). For example some two-part peroxide bleaching compositions may have a shelf-life of about 10-14 days after mixing, some disinfecting solutions may have a shelf-life of about a week or less, and some two-part dental primers may have a shelf life of about 30 days. Container systems including activatable time sensitive marking means according to the present invention are particularly suitable for use with such mixed dental compositions.

In addition, relatively stable single part dental compositions may have a shelf-life that is much longer (e.g., from 6 months up to 2 years or more). Such compositions often include an expiration date stamped or printed on the container, which can be difficult to identify. The time sensitive marking means of the present invention provides a more easily used system including a more easily identifiable label, eliminating the need for the user to search for a difficult to find date stamp. The container systems of the present invention may also be used with such compositions.

III. Exemplary Pre-Dosed, Pre-Packaged Mixing Systems

In an alternative embodiment, an initially separate two-part dental composition may be provided as a pre-dosed, pre-packaged mixing solution in which the dental practitioner is able to record a mixing and/or expiration date of the less stable mixed composition on the mixing system itself. Providing a pre-dosed, pre-packaged mixing system advantageously eliminates any need for the dental practitioner to measure the required quantities of each component prior to preparing the two-part composition. In addition to being convenient, because the pre-dosing is done during manufacture, it is advantageously accomplished with a greater degree of precision and accuracy. This reduces or eliminates the possibility of mistakes or errors in the measured quantities of each component affecting the required ratio of the first component relative to the second component. This is particularly helpful as errors in the mixing ratio may drastically affect the actual shelf-life of the mixed composition. For example, a mixed dental priming composition may have a nominal shelf-life of about 30 days after mixing, but because of a small error (e.g., ±10%) in mixing ratio, the actual shelf-life of the composition may be greatly reduced (e.g., to less than 15 days). If the composition is used after its actual expiration but before the nominal expiration, the composition will be ineffective, resulting in waste and frustration for both the dental practitioner and patient. In other words, the indicated expiration date is much more meaningful in the context of a pre-dosed, pre-packaged mixing system as compared to any other system where individual measurement of one or more of the components is required.

Figure 5A:
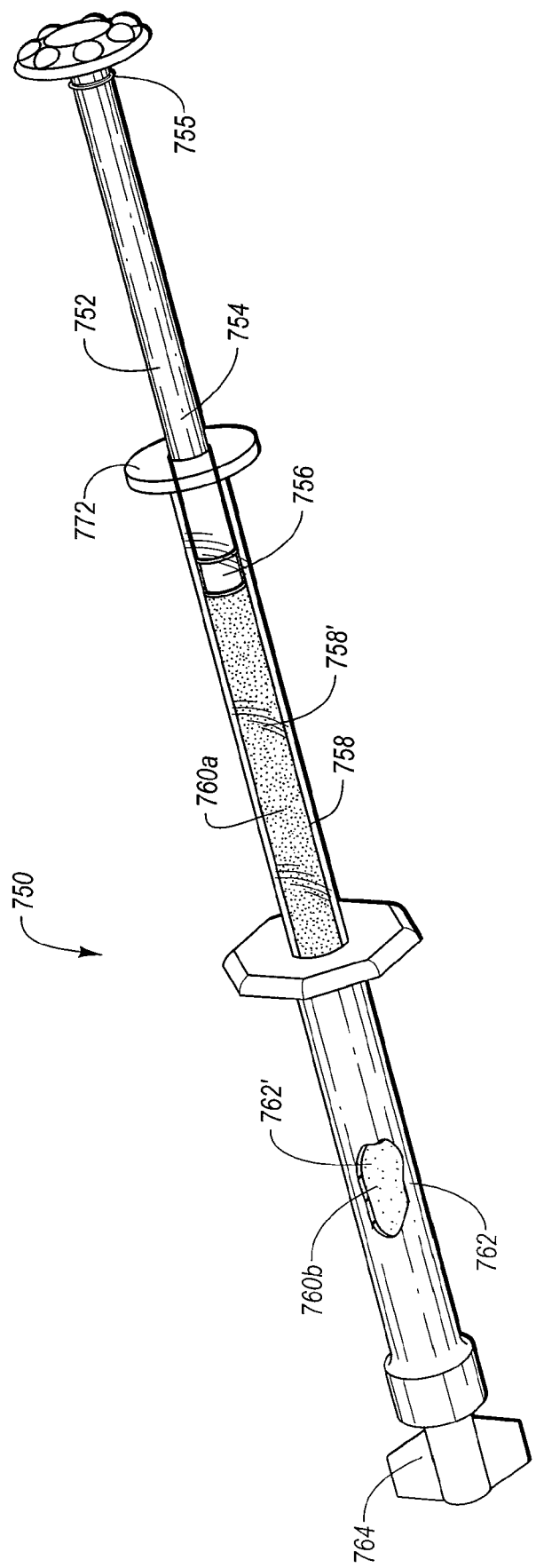
FIG. 5A illustrates an exemplary pre-dosed, pre-packaged syringe-in-syringe mixing system for use in an exemplary method of the present invention.

FIG. 5A illustrates an exemplary syringe-in-syringe mixing system 750 including a pre-dosed, pre-packaged quantity of first and second components 760a and 760b, respectively. Components 760a and 760b may both be liquids, or one component may comprise a powder, as dictated by the chemistry of the particular two-part composition. Mixing system 750 includes a first plunger 752, a second hollow plunger 758, and a syringe barrel 762. First plunger 752 includes an elongate stem 754 with a sealing plug 756 disposed at the distal end of stem 754. A locking structure 755 may be disposed near proximal end of stem 754. Locking structure 755 and its function will be described in further detail below. Plug 756 forms a seal against an interior surface of second hollow plunger 758, within which first plunger 752 is slidably disposed. A first component 760a is contained within a first chamber 758' defined by second hollow plunger 758. Second hollow plunger 758 is concentrically and slidably disposed within syringe barrel 762, which defines a second chamber 762' in which is contained a second component 760b. A cap 764 may be coupled to a distal end of syringe barrel 762, which can be removed and/or replaced with a dispensing tip for dispensing after mixing the two-part composition.

Figure 5B:
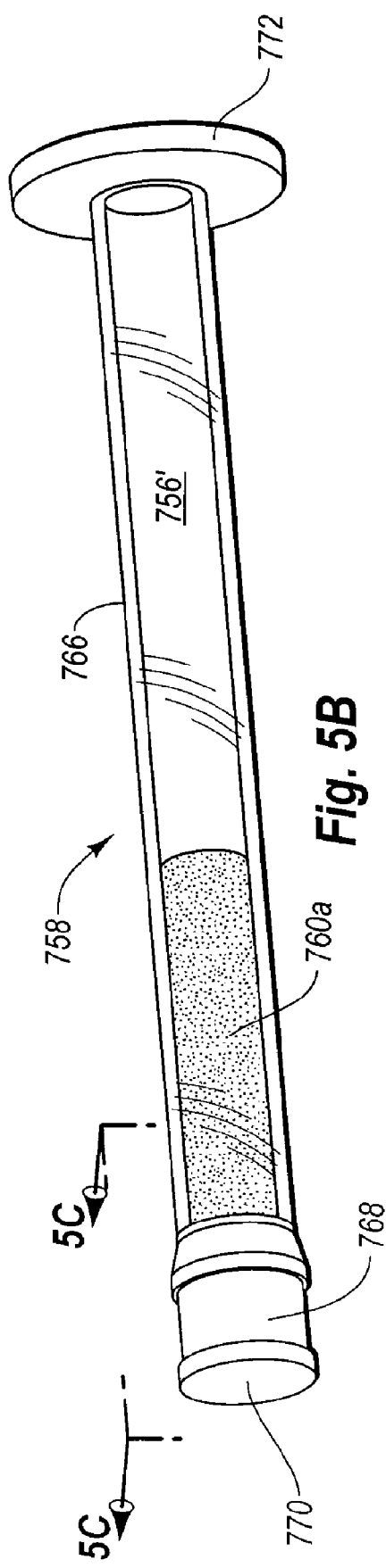
FIG. 5B illustrates a perspective view of the second hollow plunger of the syringe-in-syringe mixing system of FIG. 5A.
Figure 5C:
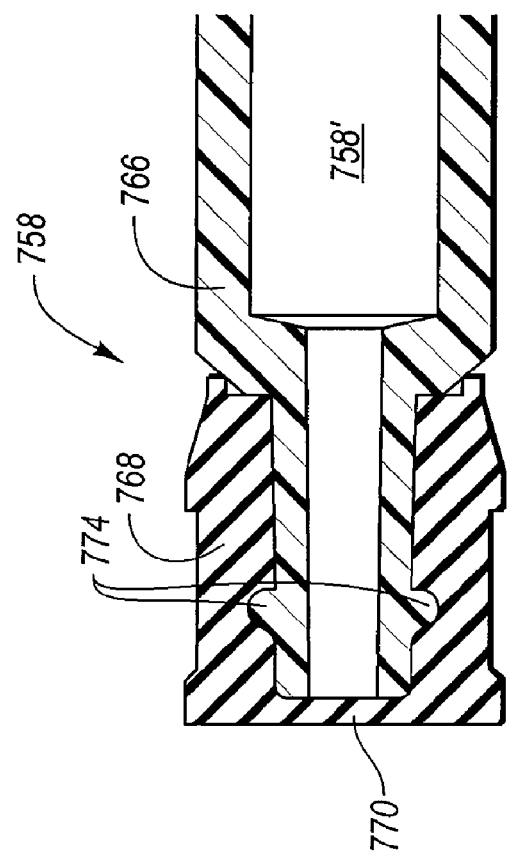
FIG. 5C illustrates a cross-sectional view of a portion of the second hollow plunger of the syringe-in-syringe mixing system of FIG. 5B, the cross-section taken along line 5C-5C.

Referring to FIGS. 5B and 5C, second hollow plunger 758 includes a wall 766 that defines an internal chamber 758' which contains a first component 760a. Second hollow plunger 758 also includes a second sealing plug 768 having a rupturable membrane 770 or other separation means (e.g., a duck bill or other type valve) at a distal end of second hollow plunger 758, and a flange 772 at a proximal end of second hollow plunger 758. Rupturable membrane 770 seals off the distal end of second hollow plunger 758, separating first component 760a from the second component 760b contained within the syringe barrel 762 (see FIG. 5A) until the user intentionally ruptures membrane 770 (or otherwise forces first component 760a through the separation means), causing first component 760a to be forced into syringe barrel 762, where the two components are mixed together. As seen in FIG. 5C, rupturable membrane 770 initially seals off a distal end of second hollow plunger 758. The distal portion of second hollow plunger 758 over which sealing plug 768 is fitted advantageously includes an enlarged annular ridge 774 that prevents plug 768 from being separated from second hollow plunger 758 during rupture of rupturable membrane 770.

Sealing plug 768 and rupturable membrane 770 may advantageously be formed of a thermoplastic elastomer (TPE) material, which advantageously provides an excellent seal against an interior surface of syringe barrel 762, while also providing a desired strength to rupturable membrane 770. Advantageously, the system may be configured so that the force required to rupture membrane 770 is approximately equal to the force required to insert and engage the locking structure 755 of first plunger 752 into second hollow plunger 758. Such a configuration advantageously provides a smooth and continuous movement and feel during use of the system as first plunger 752 is pressed into second hollow plunger 758, rupturing membrane 770 and locking first plunger 752 into second hollow plunger 758.

Rupturable membrane 770 preferably has a thickness ranging from about 0.0005 inch to about 0.04 inch, more preferably from about 0.002 inch to about 0.025 inch, and most preferably from about 0.005 inch to about 0.015 inch. Of course, the actual thickness of rupturable membrane 770 will depend on the strength and other physical properties of the material from which it is formed, along with the configuration and desired level of force required to break the membrane 770 and/or engage the optional locking structure 755. One particularly suitable material from which to form sealing plug 768 and rupturable membrane 770 is ENGAGE, a TPE material sold by DuPont-Dow Elastomers located in Wilmington, Del.

Figure 6:
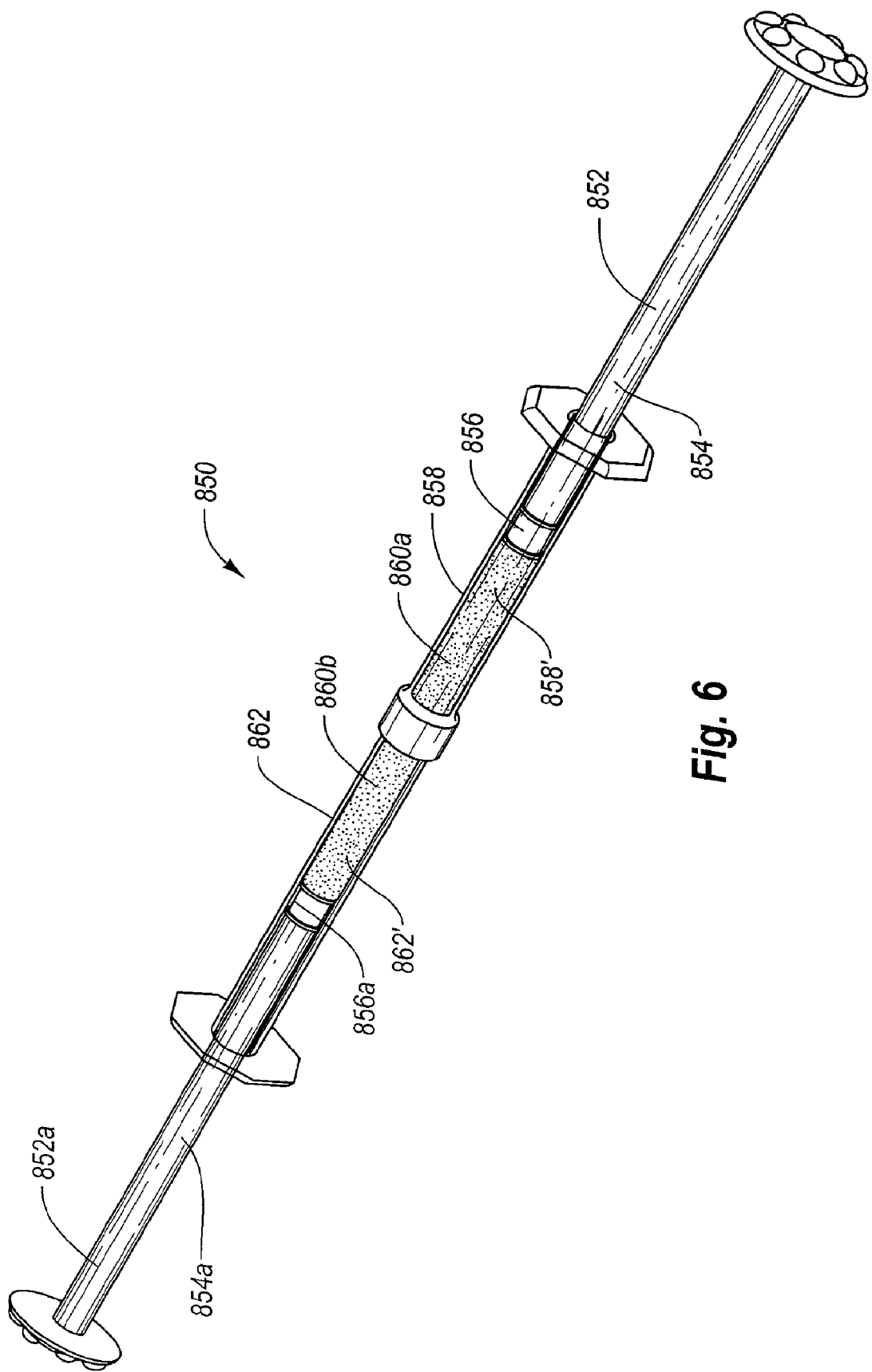
FIG. 6 illustrates an alternative pre-dosed, pre-packaged syringe-to-syringe mixing system for use in an exemplary method of the present invention.

FIG. 6 illustrates an alternative syringe-to-syringe mixing system 850 including a pre-dosed, pre-packaged quantity of first and second components. Mixing system 850 includes a first plunger 852, a first syringe barrel 858, a second plunger 852a and a second syringe barrel 862. First and second plungers 852 and 852a may be identical, each including an elongate stem 854, 854a with a sealing plug 856, 856a, respectively, formed at the distal end of stems 854, 854a. Each of plugs 856, 856a forms a seal against an interior surface of syringe barrels 858 and 862, respectively, within which each of plungers 852, 852a is slidably disposed.

First syringe barrel 858 defines an internal first chamber 858' in which is contained a pre-dosed, pre-packaged quantity of first component 860a. Similarly, second syringe barrel 862 defines an internal second chamber 862' in which is contained a pre-dosed, pre-packaged quantity of second component 860b. Separation means (e.g., a rupturable membrane, duck bill valve, or other type valve) is disposed (not shown) between first chamber 858' and second chamber 862' so as to initially separate first and second components 860a and 860b during storage and prior to use, as any premature mixing may result in a partially mixed, less stable composition, which quickly becomes ineffective and useless. An example of such separation means is the plug and rupturable membrane illustrated in conjunction with FIGS. 5B and 5C. In another example, the separation means may comprise a small film of rupturable polymeric or other material (e.g., similar to SARAN wrap) stretched or otherwise disposed over the distal end of one or both of syringe barrels 858 or 862, which acts to initially separate chamber 858' from 862'.

In order to mix the two-part composition, the user presses one of the plungers (e.g., first plunger 852) in, so as to force the component contained within the associated syringe barrel (e.g., first syringe barrel 858) through a rupturable membrane or other separation means and into the other syringe barrel (e.g., second syringe barrel 862). In order to further mix the components so as to form a homogeneous mixture, the other plunger (e.g., second plunger 852a) may then be pressed in, forcing the intermingled first and second components back into the other syringe barrel (e.g., first syringe barrel 858). The plungers may be alternatingly pressed as many times as needed (e.g., about 3-10 times) so as to cycle the two-part composition back and forth, effecting homogeneous mixing.

IV. Exemplary Methods of Use

In one exemplary method of use, a dental composition having a given shelf-life is provided. For example, the dental composition may comprise a mixed composition formed by mixing together initially separate components in a syringe-to-syringe mixing device or other suitable mixing apparatus. A container including activatable time sensitive marking means disposed on or within the container is also provided. The container may comprise a syringe of the syringe-to-syringe mixing apparatus such that the dental composition may be contained within the syringe or other container. Alternatively, the dental composition may be introduced into the container (e.g., a syringe) including an activatable time sensitive marking means disposed on or within the container.

The time sensitive marking means may be activated when needed so as to begin to indicate the remaining shelf-life of the composition. Typically the time of activation will coincide with an event which affects the shelf-life of the composition (e.g., mixing initially separate components to form the dental composition or opening a container to expose the dental composition to air or light). The time sensitive marking means indicates how much time has lapsed since activation, indicating to the user whether the dental composition is usable or not.

The dental practitioner identifies whether the given shelf-life of the composition is greater than or less than the time lapsed since activation. If the lapsed time is less than the given shelf-life, then the dental practitioner may dispense and use the dental composition. If the given shelf-life is less than the time lapsed since activation, then the dental practitioner may discard the composition or system. The container and activatable time sensitive marking means may be relatively inexpensive, allowing the user to discard the entire system once the dental composition has expired.

FIGS. 7A-7D illustrate an alternative method for indicating shelf-life employing the exemplary pre-dosed, pre-packaged syringe-in-syringe mixing system 750 of FIG. 5A. A syringe-to-syringe mixing system (e.g., mixing system 850 of FIG. 6) may alternatively be used according to a similar method to provide a dental practitioner with an easy to use mixing solution that indicates shelf-life of the less stable mixed dental composition. Advantageously, such systems provide a pre-dosed and pre-packaged system that may be used for mixing, dispensing, and storing the mixed two-part composition. Furthermore, such systems provide a pre-dosed, pre-packaged mixing solution in which the two components are pre-measured in the correct quantities for mixing a desired quantity of the two-part composition. Pre-dosing and pre-packaging the components reduces the work required of the dental practitioner, and reduces the possibility that a user (particularly an inexperienced one) will make a mistake in measuring quantities of the components (i.e., affecting the mixing ratio), which may drastically alter the effectiveness and/or shelf-life of the mixed composition. In addition, the pre-packaged amount of each component may advantageously be sufficient (and no more) so as to provide a quantity of the mixed two-part composition that would typically be used up by the dental practitioner within the specific shelf-life of the mixed, unstable two-part composition so as to reduce waste of any unused composition. For example, the amounts of each component may be such as to prepare between about 0.05 and about 1 mL, more typically between about 0.1 and about 0.8 mL, and most typically between about 0.2 and about 0.6 mL of the less stable mixed dental composition. The actual amount of mixed dental composition depends on the particular composition (e.g., a dental primer, a peroxide or other two-part bleaching composition, or a disinfecting solution), as different compositions are used more or less frequently in various amounts, and each composition also has its own particular shelf life (e.g., less than about 90 days, less than about 30 days, or less than about 2 weeks). Providing no more than a quantity sufficient for the shelf-life of the composition is advantageous as the amount mixed is used up within the particular shelf life of the composition, which reduces waste.

Figure 7A:
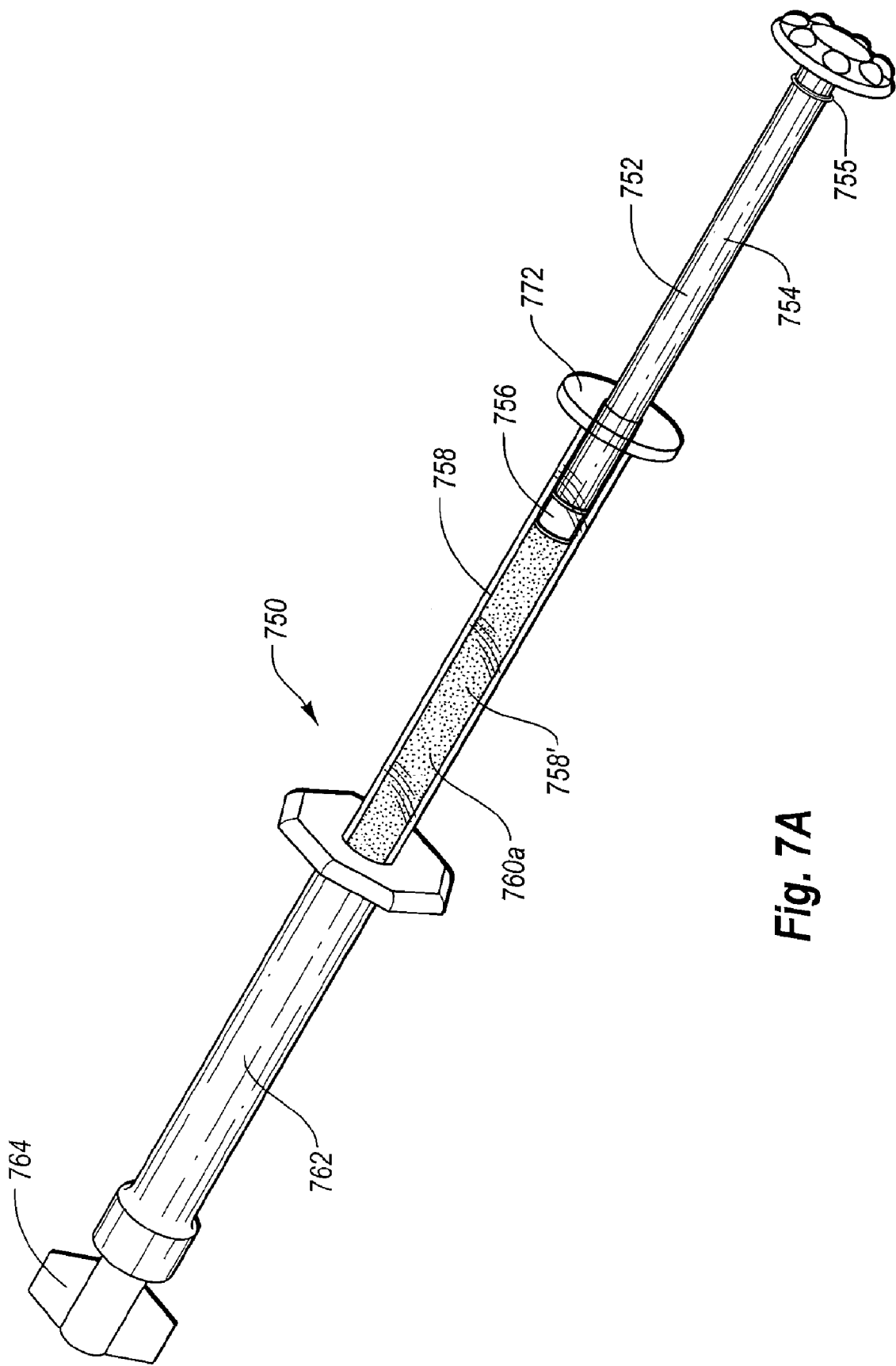
FIG. 7A illustrates the exemplary pre-dosed, pre-packaged syringe-in-syringe mixing system of FIG. 5A prior to mixing.
Figure 7B:
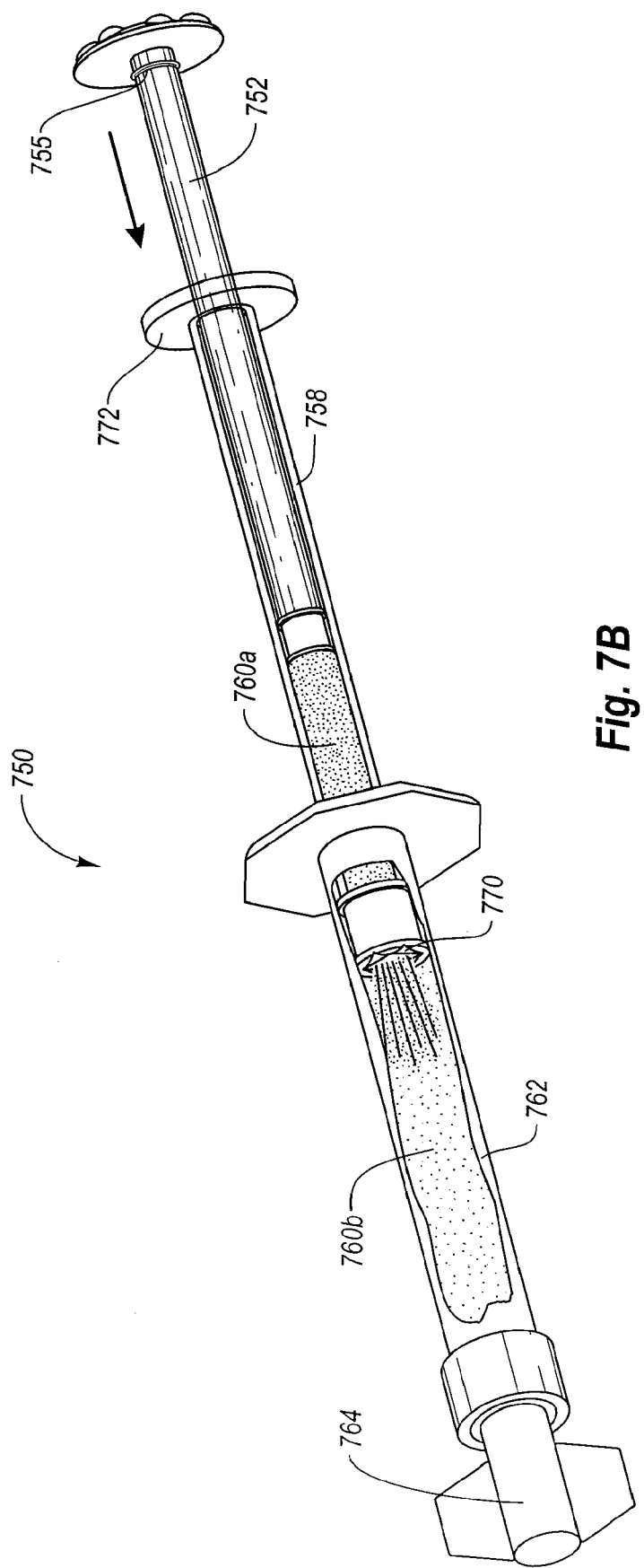
FIG. 7B illustrates the mixing system of FIG. 7A when the first plunger is pressed in so as to break the rupturable membrane, causing mixing of the two components.
Figure 7C:
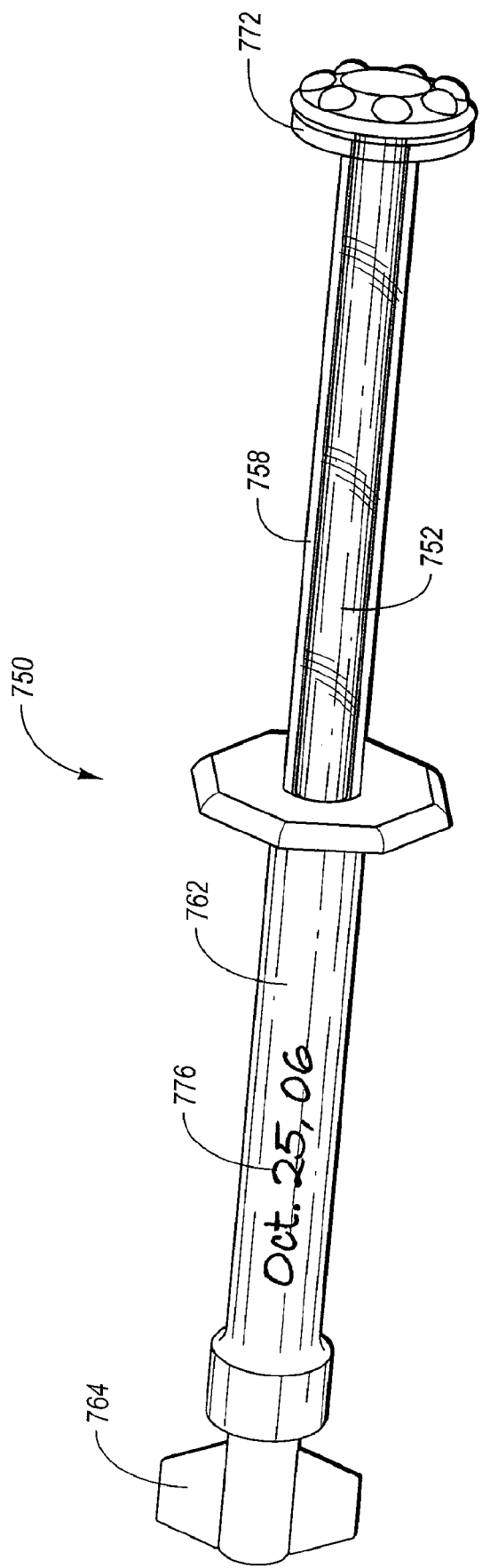
FIG. 7C illustrates the mixing system of FIG. 7B once the first plunger is fully inserted into the second hollow plunger, and a mixing and/or expiration date has been written on an exterior surface of the syringe barrel.

As seen in FIGS. 7B-7C, the user presses first plunger 752 into second hollow plunger 758 so as to compress first component 760a. Once a sufficient force is applied, first component 760a is expressed under pressure from second hollow plunger 758 into syringe barrel 762 where it mixes with second component 760b, which may occur through rupture of rupturable membrane 770 or breaking, opening, and/or parting of some other separation means.

Rupturable membrane 770, a valve, or other separation means may advantageously be configured to only pass first component 760a for mixing with second component 760b under a pressure sufficiently high to cause jetting of the first component into the second component (e.g, so as to create turbulence sufficient to homogeneously mix the two components together). The system may advantageously be configured such that a force required to rupture membrane 770 is approximately equal to a force required to insert and lock locking structure 755 into second hollow plunger 758. In use, locking structure 755 becomes inserted into second hollow plunger 758, where the locking structure 755 biases against the inside surface of second hollow plunger 758. Such an optional locking structure results in a configuration such that when first plunger 752 is fully inserted into second hollow plunger 758, locking structure 755 extends distally into second hollow plunger 758, past flange 772. Locking structure 755, illustrated as comprising an annular interlock ring, causes the formation of an indentation or groove within the inside wall of second hollow plunger 758. Annular interlock ring locking structure 755 resides in the formed groove, preventing, or at least inhibiting, pull out of first plunger 752 once fully inserted into second hollow plunger 758. Additional locking structures and mixing systems are disclosed in U.S. patent application Ser. No. 11/414,964, filed May 1, 2006, already incorporated by reference, and in U.S. patent application Ser. No. 11/537,883, filed the same day as the present application, which is also incorporated by reference in its entirety.

As seen in FIG. 7C, the user is able to record the mixing and/or expiration date 776 on a surface of mixing system 750 either immediately prior to or immediately subsequent to fully pressing first plunger 752 into second hollow plunger 758. As illustrated, the user may write a mixing and/or expiration date directly onto the exterior surface. Advantageously, a designated exterior writing surface (e.g., at least a portion of the syringe barrel) may be coated or otherwise comprise a textured surface comprising a TPE material, which provides an improved writing surface on which a ball-point pen or similar writing device can be used (i.e., the TPE material acts to "grab" the writing end of a ball-point pen). Of course a felt-tip pen, marker, or even a pencil may also be used. Alternatively, the date may be written on a label (e.g., a pressure sensitive adhesive label) which is adhered to the exterior surface of the syringe barrel 762. Advantageously, the dental practitioner may apply a transparent or translucent adhesive protective covering (e.g., SCOTCH tape) over the recorded date so as to protect the date from damage or alteration (e.g., by contact with a solvent, by smearing, or rubbing which may otherwise wear away the date or render it illegible).

Figure 7D:
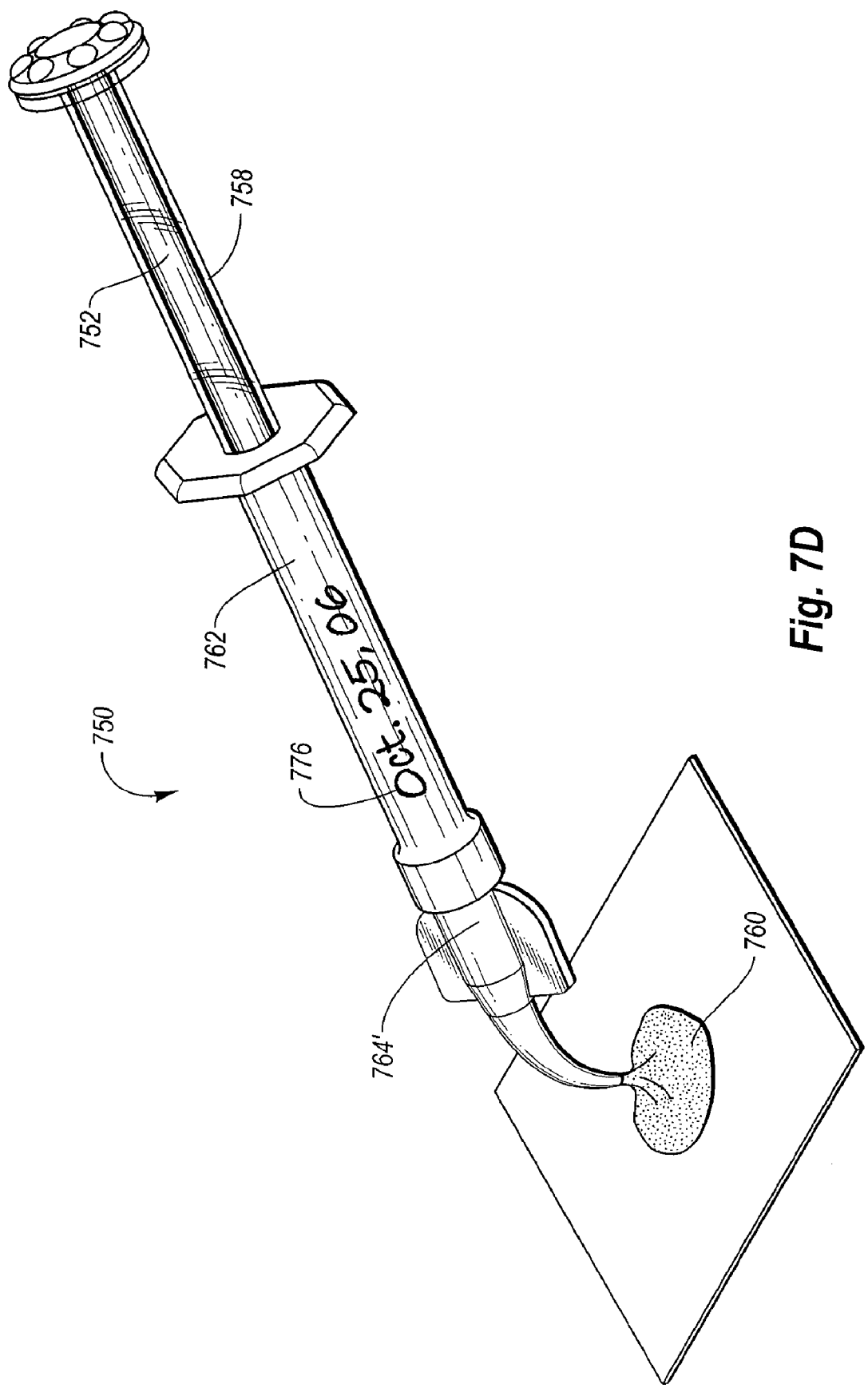
FIG. 7D illustrates the mixing system coupled to a dispensing tip and a portion of the less stable mixed dental composition being dispensed onto a surface for use.

Advantageously, the mixing system 750 may be used for storing and dispensing the mixed composition, so that no transfer to a separate dispensing device is required. FIG. 7D illustrates the system 750 with a dispensing tip 764' coupled at a distal end of barrel 762 so as to allow the user to dispense the mixed two-part composition 760. As illustrated, composition 760 may be dispensed onto a pad for subsequent application (e.g., with a brush tool). Alternatively composition 760 may be dispensed directly onto a tooth or other surface, depending on the preference of the user.

The inventive method advantageously provides a simple, ready to use system in which the two-part composition is provided in a pre-dosed, pre-packaged, ready to mix and use configuration. In addition, the user is able to record the mixing and/or expiration date directly onto a surface of the mixing system for later reference, indicating to the dental practitioner whether the less stable mixed dental composition has expired or not. The system and associated method reduces or eliminates the possibility of mistakes or errors in the measured quantities of each component affecting the required mixing ratio and actual shelf-life of the mixed composition.

It will be appreciated that the present claimed invention may be embodied in other specific forms without departing from its spirit or essential characteristics. For example, although several specific embodiments of activatable time sensitive marking means have been described, it is to be understood that any structure that can be disposed on or integrated into the container with the ability to indicate time lapsed since activation may be used. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A syringe system for mixing and for recording the mixing date to permit monitoring of the shelf life of a mixed two-part dental composition, the syringe system comprising:
   a first pre-dosed composition pre-packaged so as to be contained in a first syringe having a barrel with a first plunger slidable within the first barrel;
   a second pre-dosed composition pre-packaged so as to be contained in a second syringe having a barrel, with a second plunger slidable within the second barrel, and the separate compositions each having a shelf life significantly greater than the shelf life of the two compositions after they are mixed;
   the first and second plungers being operable so that by first sliding the first plunger into the first syringe barrel the first pre-dosed composition is introduced into the second syringe barrel so that it contacts the second pre-dosed composition, the two compositions thereafter being either further mixed using one or both syringe barrels, or else applied in a dental procedure by expressing the mixed contents from the second syringe barrel; and
   time and temperature sensitive marking means, disposed on one of the first or second syringes, which, when activated upon mixing the two compositions, thereafter provides a visual indication which automatically changes over time so as to indicate the lapsed time and temperature conditions from when the two compositions were mixed, and which also changes as a function of temperature, so that the shelf life of the mixed compositions is easily ascertainable from the visual indication.

2. The system of claim 1 wherein the time sensitive means comprises an activatable label having a length of microporous material and a tinted liquid contained within a sealed blister, such that when the blister is activated to release the liquid, it will migrate along the length of the microporous material as a function of time that shows how much time has lapsed since the two compositions were mixed, and thus how much shelf life remains for the mixed compositions.

3. The system of claim 1 wherein the time sensitive means comprises first and second compositions contained in first and second sealed blisters, respectively, that are separated by a membrane which, when broken, activates mixing of the first and second compositions in the two blisters by mixing them, so that thereafter the mixed compositions create a first color that progressively changes to a second color over time, the second color indicating elapsed time and thus the end of the shelf life of the mixed dental compositions.

4. The system of claim 3, wherein the rate at which the mixed compositions change color from the first to the second color will be delayed when the mixed dental compositions are refrigerated to extend the shelf life of the mixed dental compositions.

5. The system of claim 1 wherein the time sensitive means comprises an activatable label having a material which, when exposed by pealing back a cover, begins to change from a first to a second color as a function of time, the second color indicating elapsed time and thus the end of the shelf life of the mixed dental compositions.

6. The system of claim 5, wherein the rate at which the material of the label changes color from the first to the second color will be delayed when the mixed dental compositions are refrigerated to extend the shelf life of the mixed dental compositions.

7. The system of claim 1 wherein the time sensitive means comprises an activatable label having a microchip readable by an associated microchip reader which indicates to a user the time lapsed since mixing the two dental compositions.

8. The system of claim 7 wherein the microchip is configured to account for differences in temperature so that the lapsed time recorded by the microchip will be delayed when the mixed dental compositions are refrigerated to extend the shelf life of the mixed dental compositions.

9. The system of claim 1 wherein the first syringe barrel is connected end-to-end with the second syringe barrel so as to form a syringe-to-syringe mixing system.

10. The system of claim 1 wherein the first syringe barrel fits within the second syringe barrel so that the first syringe barrel also functions as the plunger for the second syringe barrel, thus forming a syringe-in-syringe mixing system.

11. The system of claim 10 wherein an outlet end of the first syringe barrel comprises a rupturable membrane so that when the plunger is pushed into the first syringe barrel, the pre-dosed dental composition packaged within the first syringe barrel will be expelled under pressure sufficient to create turbulence, into the second syringe barrel, thus mixing the two dental compositions in the second syringe barrel.

12. The system of claim 10 wherein the plunger of the first syringe barrel comprises a locking structure so that when the plunger is pushed into the first syringe barrel a sufficient distance, the syringe plunger inhibits the plunger from thereafter being withdrawn from the first syringe barrel.

13. The system of claim 12 wherein the locking structure comprises an annular ring formed on a circumference of the plunger of the first syringe barrel which cooperates with a corresponding groove formed inside the first syringe barrel for receiving the annular ring when the plunger is pushed far enough into the first syringe barrel.

14. In a syringe system for mixing for recording the mixing date to permit monitoring of the shelf life of a mixed two-part dental composition, a method comprising steps for:
provide a first pre-dosed composition pre-packaged so as to be contained in a first syringe having a barrel with a first plunger slidable within the first barrel;
providing a second pre-dosed composition pre-packaged so as to be contained in a second syringe having a barrel, with a second plunger slidable within the second barrel, and the separate compositions each having a shelf life significantly greater than the shelf life of the two compositions after they are mixed;
providing a time sensitive and temperature-dependent marking means, disposed on one of the first or second syringes;
operating the first and second plungers so that by first sliding the first plunger into the first syringe barrel the first pre-dosed composition is introduced into the second syringe barrel so that it contacts the second pre-dosed composition, the two compositions thereafter being either further mixed using one or both syringe barrels, or else applied in a dental procedure by expressing the mixed contents from the second syringe barrel;
upon mixing the two dental composition, activating the time and temperature sensitive markings, means in order to provide a visual indication which automatically changes over time so as to indicate the lapsed time and temperature conditions from when the two compositions were mixed, so that the shelf life of the mixed compositions is easily ascertainable from the visual indication.

15. The method of claim 14 wherein the time sensitive means comprises an activatable label having a length of microporous material and a tinted liquid contained within a sealed blister, and wherein the step for activating the label comprises bursting the sealed blister to release the liquid, so that the liquid will then migrate along the length of the microporous material as a function of time that shows how much time has lapsed since the two compositions were mixed, and thus how much shelf life remains for the mixed compositions.

16. The method of claim 14 wherein the time sensitive means comprises first and second compositions contained in first and second sealed blisters, respectively, that are separated by a membrane, and wherein the step for activating the label comprises bursting at least one of the blisters to cause mixing of the first and second compositions in the two blisters, so that thereafter the mixed compositions create a first color that progressively changes to a second color over time, the second color indicating elapsed time and thus the end of the shelf life of the mixed dental compositions.

17. The method of claim 16, wherein the rate at which the mixed compositions change color from the first to the second color will be delayed when the mixed dental compositions are refrigerated to extend the shelf life of the mixed dental compositions.

18. The method of claim 1 wherein the time sensitive means comprises an activatable label having a color-changing material, and wherein the step for activating the label comprises pealing back a cover to expose the color-changing material to that it begins to change from a first to a second color as a function of time, the second color indicating elapsed time and thus the end of the shelf life of the mixed dental compositions.

19. The method of claim 18, wherein the rate at which the material of the label changes color from the first to the second color will be delayed when the mixed dental compositions are refrigerated to extend the shelf life of the mixed dental compositions.

20. The method of claim 14 wherein the time sensitive means comprises an activatable label having a microchip readable by an associated microchip reader, and wherein the step for activating the label comprises initiating the microchip so that it indicates to a user the time lapsed since mixing the two dental compositions.

21. The method of claim 20 wherein the microchip is configured to account for differences in temperature so that the lapsed time recorded by the microchip will be delayed when the mixed dental compositions are refrigerated to extend the shelf life of the mixed dental compositions.

22. The method of claim 14 wherein the first syringe barrel is connected end-to-end with the second syringe barrel so as to form a syringe-to-syringe mixing system, and wherein the step for operating the first and second plungers comprises sliding the first plunger into the first syringe barrel at one end of the syringe barrels that are connected end-to-end, and then sliding the second plunger at the opposite end of the connected syringe barrels into the second syringe barrel so that the two dental compositions are mixed as they move back and forth from one syringe barrel into the other.

23. The method of claim 14 wherein the first syringe barrel fits within the second syringe barrel so that the first syringe barrel also functions as the plunger for the second syringe barrel, thus forming a syringe-in-syringe mixing system, and wherein the step for operating the first and second plungers comprises sliding the first plunger into the first syringe barrel and then using the first syringe barrel as a plunger for the second syringe barrel, sliding the first syringe barrel into the second syringe barrel to either further mix or else expel the mixed contents, as desired.

24. The method of claim 23 wherein an outlet end of the first syringe barrel comprises a rupturable membrane so that when the plunger is pushed into the first syringe barrel, the pre-dosed dental composition packaged within the first syringe barrel will be expelled under pressure sufficient to create turbulence, into the second syringe barrel, thus mixing the two dental compositions in the second syringe barrel.

25. The method of claim 23 wherein the plunger of the first syringe barrel comprises a locking structure so that when the plunger is pushed into the first syringe barrel a sufficient distance, the syringe plunger inhibits the plunger from thereafter being withdrawn from the first syringe barrel, and wherein the method further comprises locking the plunger of the first syringe barrel into the first syringe barrel.

26. The method of claim 25 wherein the locking structure comprises an annular ring formed on a circumference of the plunger of the first syringe barrel which cooperates with a corresponding groove formed inside the first syringe barrel for receiving the annular ring when the plunger is pushed far enough into the first syringe barrel, and wherein locking the plunger of the first syringe barrel into the first syringe barrel comprises pushing the plunger far enough into the first syringe barrel so that the annular ring mates with the annular groove.

* * * * *

UNITED STATES PATENT AND TRADEMARK OFFICE
CERTIFICATE OF CORRECTION

PATENT NO. : 7,569,185 B2  Page 1 of 1
APPLICATION NO. : 11/537807
DATED : August 4, 2009
INVENTOR(S) : Fischer It is certified that error appears in the above-identified patent and that said Letters Patent is hereby corrected as shown below:

Column 3
Line 55, change "more full apparent" to --more fully apparent--

Column 6
Line 48, change "barrel 314" to --barrel 314'--

Column 14
Claim 5, line 25, change "pealing" to --peeling--

Column 15
Claim 14, line 1, change "for mixing for recording" to --for mixing and for recording--
Claim 14, line 24, change "two dental composition" to --two dental compositions--
Claim 18, line 59, change "pealing" to --peeling--
Claim 18, line 60, change "material to that" to --material so that--

Signed and Sealed this

First Day of December, 2009

David J. Kappos
*Director of the United States Patent and Trademark Office*